Figure 1:
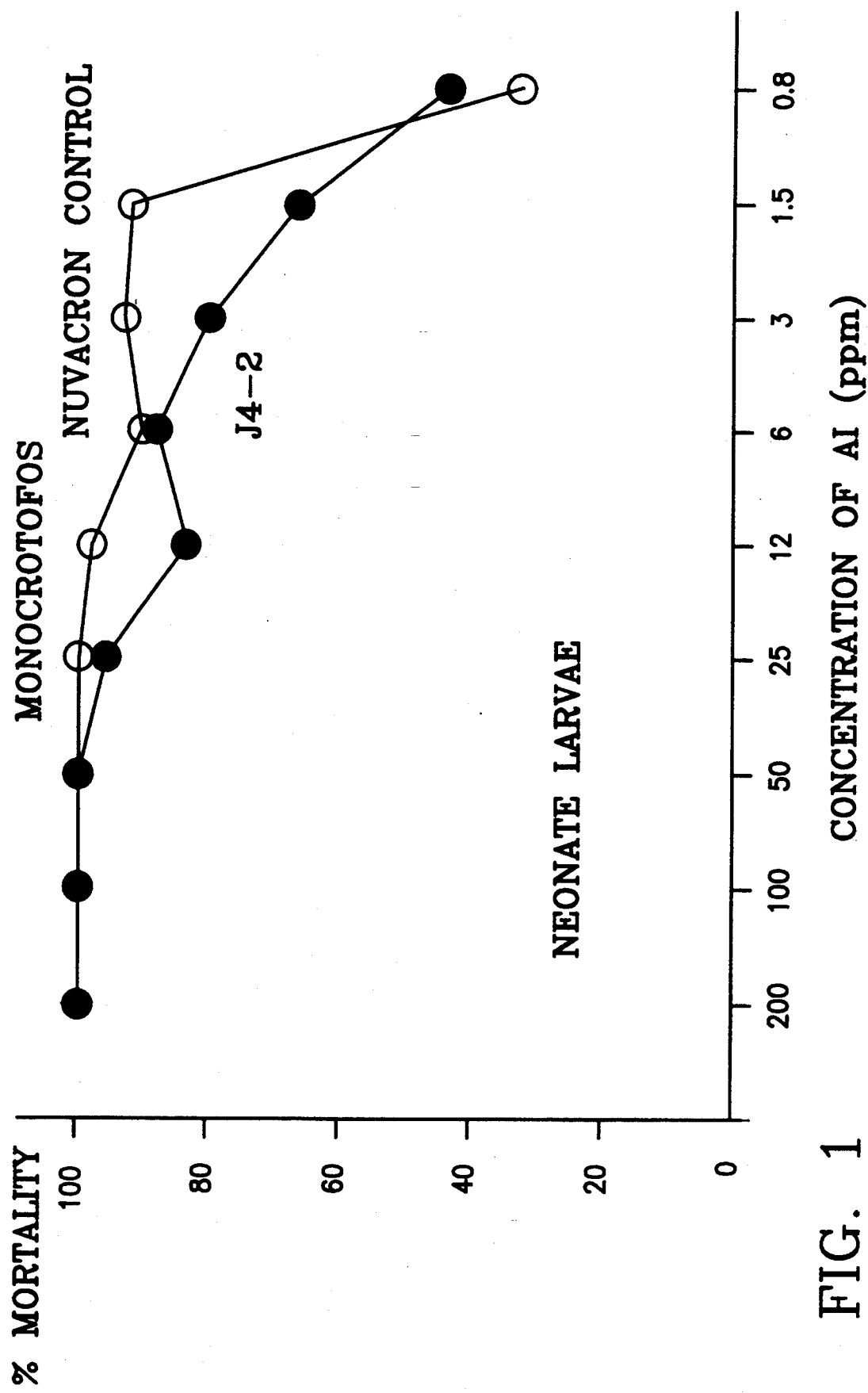

United States Patent [19]

Harrington

[11] Patent Number: 5,366,961

[45] Date of Patent: Nov. 22, 1994

[54] PESTICIDAL PRODUCTS

[75] Inventor: Kevin J. Harrington, East Bentleigh, Australia

[73] Assignee: Commonwealth Scientific and Industrial Research Organisation, Campbell, Australia

[21] Appl. No.: 961,697

[22] PCT Filed: Aug. 13, 1991

[86] PCT No.: PCT/AU91/00360

§ 371 Date: Apr. 2, 1993

§ 102(e) Date: Apr. 2, 1993

[87] PCT Pub. No.: WO92/03048

PCT Pub. Date: Mar. 5, 1992

[30] Foreign Application Priority Data

Aug. 13, 1990 [AU] Australia ............. PK1700/90

[51] Int. Cl.$^5$ ............................................. A01N 25/32
[52] U.S. Cl. .................................. 514/53; 71/DIG. 1; 71/DIG. 2; 47/DIG. 10; 47/DIG. 11; 424/405
[58] Field of Search ................... 71/DIG. 1, DIG. 2; 47/DIG. 10, DIG. 11; 424/405, 409; 514/53

[56] References Cited

U.S. PATENT DOCUMENTS

| 3,920,442 | 11/1975 | Albert et al. | 71/92 |
| 3,983,214 | 9/1976 | Misato et al. | 424/405 |
| 4,241,054 | 12/1980 | Volpenhein et al. | 424/405 |
| 4,541,859 | 9/1985 | Tozawa et al. | 514/53 |
| 4,665,059 | 5/1987 | Tozawa et al. | 514/53 |
| 4,666,706 | 5/1987 | Farquharson et al. | 424/408 |

Primary Examiner—Ronald W. Griffin
Attorney, Agent, or Firm—Bacon & Thomas

[57] ABSTRACT

A pesticidal material which comprises an inclusion compound or a molecular complex of a pesticide and a host molecule characterized in that the host molecule is a mono-, oligo- or polysaccharide ester. A pesticidal composition and a method for combatting insect pests involving the above pesticidal material are also described.

10 Claims, 2 Drawing Sheets

PESTICIDAL PRODUCTS

This invention relates to new forms of pesticidal products and methods for their manufacture.

Environmental awareness of the dangers of pollution arising from the widespread application of chemical pesticides, as well as the increased cost of developing and registering new pesticides, has stimulated interest in developing formulations that will improve the effectiveness of present pest control agents by, for example, improving their shelf life and increasing their stability and longevity of action in the field. There is also a need to minimise the health and environmental hazards associated with the use of common pesticides such as organophosphates and toxic metallic compounds.

Typical formulations used to apply known pesticides include dusts and sprays. Dusts are often used to control termites, cockroaches, lepidopterous larvae, grain insects, ants and other urban and rural pests. Sprays, which include emulsions and wettable powders, are extensively employed in combating agricultural crop insect pests of cotton, grain, rice, sugar, tobacco, vegetables and fruits as well as wood destroying insects such as termites and wood bores. However, the effectiveness of many pesticide applications is often markedly reduced by factors such as loss of the active ingredient by evaporation, its hydrolysis or inactivation in the presence of moisture or when in contact with soil, and degradation of the pesticide through the action of light. This lack of persistence may make repeated applications essential to ensure continued and adequate pest control.

A further problem in the control of insect pests is that insects can often detect the toxic agents used to the extent that they are repelled and avoid ingesting or coming into contact with the toxicant.

For many years pest control operators in Australia have used arsenic trioxide to eradicate termite infestations in and around buildings. The arsenical compound is normally puffed into the galleries created by the termites in infested wood, causing the toxic dust to adhere to the termites' cuticle and appendages such an antennae, legs and hair. This very effective method exploits the insects' behavioural characteristics of social grooming and dead termite control. During the grooming ritual, traces of toxic dust may be ingested by the grooming insect, which will eventually die. Dead termites are eaten by survivors who themselves soon become victims, thus aiding in the translocation of the poison throughout the colony.

However, the distribution of arsenical compounds having a wide spectrum of insecticidal and mammalian toxicity is undesirable, and the alleged carcinogenicity of arsenic, particularly in its trivalent oxidised state, has resulted in a ban on its use for termite eradication in the U.S.A. Similar restrictions may be imposed in Australia and other countries. Alternative termiticidal dusts have been proposed that rely upon adsorbing known insecticides such as organochlorins, organophosphates or synthetic pyrethroids on finely divided supports such as kaolin or talc. Such insecticidal dusts still present a considerable hazard to the pest control operator as, in most cases, the adsorbed insecticide has a measurable vapour pressure and may be adsorbed through skin contact or inhalation. Moreover, these dusts have generally been found to repel the termites, which seal off the dusted areas to avoid contact with the poison.

There have been many attempts to achieve safer and more effective use of pesticides by developing controlled release systems to allow reduced rates and frequency of application and to minimise evaporation and degradation losses. One such approach is disclosed in Australian Patent Application No. 83/13398 in which biologically active materials are trapped as discontinuous domains within a continuous insoluble matrix gel, the biodegradation of which results in slow release of the active agent. A disadvantage of this method is the difficulty of obtaining complete encapsulation in products that are sufficiently finely divided for dusting applications.

Another known method of stabilising pesticides is to form molecular complexes of the clathrate or inclusion type between the "guest" pesticide and a "host" lattice. Inclusion in organic hosts results in many modifications to the properties of the guest compounds such as fixation of volatile materials, masking of odorous compounds, stabilisation against hydrolysis, protection against oxidation and photolysis, e.g. by ultraviolet light, and the modification of their physical and biological properties.

U.K. Patent No. 1,453,801 discloses the formation of a molecular complex of the clathrate type between the general purpose organophosphate insecticide dichlorvos (DDVP) and cyclodextrins, particularly $\beta$-cyclodextrin (CD), to provide a stable formulation with powerful insecticidal effects. Similar complexes have been described between CD and methyl parathion, another organophosphate insecticide, as well as with a range of natural and synthetic pyrethroids.

Dichlorvos (DDVP) is an inexpensive, readily available but volatile and inflammable insecticide. It is also susceptible to rapid hydrolysis by alkali and water and so is devoid of long lasting effects. The DDVP-CD complex, containing 14–16% DDVP based on the mass of $\beta$-cyclodextrin, has very low volatility and reacts but slowly with moist air. However, its application to insect control is justified only under dry conditions; if the water-soluble $\beta$-cyclodextrin were to dissolve the complex would dissociate with concomitant rapid hydrolysis of the DDVP.

Cyclodextrin complexes of natural pyrethrins and synthetic pyrethroids, containing 6–15% of the toxicants, showed enhanced photostability over the free insecticides which are rapidly degraded in air and light. Persistency of the pyrethroids was enhanced at the expense of some loss in contact insecticidal activity, but the complexes retained their insecticidal activity upon ingestion by insects.

In summary, cyclodextrin-included insecticides are limited in use by cost and low persistency in wet conditions, their application being justifiable only in certain areas. It is an object of this invention to provide inclusion compounds or molecular complexes of the type in question in which one or both of the above-described disadvantages is minimised or at least reduced.

We have now found that derivatives of other types of polyhydroxylic compounds are also capable of forming inclusion compounds or molecular complexes with pesticides.

In accordance with the present invention there is provided a pesticidal material which comprises an inclusion compound or molecular complex of a mono-, oligo- or poly-saccharide ester and a pesticide.

Any suitable known mono-, oligo- or poly-saccharide may be used as the basis of the mono-, oligo- or poly-saccharide ester, for example, glucose and sucrose.

The preferred mono-, oligo- or poly-saccharide esters are mono-, oligo- or poly-saccharides esterified by carboxylic acids. The carboxylic acids may be mono-, di- or poly-basic, and may be a simple aliphatic or alicyclic carboxylic acid, of suitable carbon chain length, for example fatty acids, such as palmitic acid, or may contain various substituents including hydroxyl groups. Esters of optionally substituted aromatic carboxylic acids are also particularly suitable.

The mono-, oligo- or poly- saccharide ester may contain any number of ester groups up to the maximum permitted by the number of (esterifiable) hydroxy groups available. Preferably the maximum number of hydroxy groups is esterified.

Examples of suitable compounds are:
β-D-Glucose (penta) myristate;
Mannitol (hexa) palmitate;
Pentaerythritol (tetra) palmitate;
β-D-Glucose (penta) palmitate;
Pentaerythritol (tetra) monosuccinate;
Pentaerythritol (tetra) benzoate;
Sucrose (octa) benzoate;
Mannitol (hexa) benzoate;
β-D-Glucose (penta) cyclohexane carboxylate;
Pentaerythritol (tetra) phenylacetate;
Pentaerythritol (tetra) cyclohexane carboxylate; or
Mannitol (hexa) cyclohexane carboxylate.

Sucrose benzoate is particularly preferred.

Preferably, the inclusion compounds or molecular complexes are substantially water insoluble. Thus, it will be appreciated that the nature of the acid moiety and the degree of esterification of the mono-, oligo- or poly-saccharide will govern the solubility of the inclusion compound or molecular complex produced.

Pesticides from any of the known classes can be considered for use in accordance with this invention, provided that their molecular dimensions are such as to permit inclusion into or complexing with the mono-, or oligo- or poly-saccharide ester.

Suitable pesticides include the pyrethroid, organophosphorus and carbamate pesticides. Some suitable pesticides identified by their common names as given in "The Pesticides Manual", 7th Edition, 1983 and published by the British Crop Protection Society, include the organophosphates chlorpyrifos. dichlorvos, fenthion, fenthion ethyl, fenitrothion, fonofos, methacriphos, methomyl, monocrotofos, phoxim, and trithion, and the synthetic pyrethroids fenvalerate, permethrin and cypermethrin.

Whilst the present invention is generally described herein with reference to compounds or complexes which involve pesticide guests, the invention is not restricted to such guests. Any other guest substance may be considered for applications outside the field of insect and other pest control.

The basis and practice of the invention are further described and illustrated by the following non-limiting examples.

EXAMPLE 1

Preparation of Sucrose octa (Benzoate)

Sucrose (12.5 g, 0.037 mol) was suspended in pyridine (125 mL) and benzoyl chloride (43 ml, 0.37 mol) was added slowly with stirring. The reaction mixture was then heated to reflux temperature for 1 hour and then allowed to return to room temperature. Aqueous NaHCO$_3$ was added (430 mL, 5%) and the mixture was cooled in an ice bath to produce a gummy yellow solid. After decantation, the solid was washed several times with cold water and finally crystallised from dilute ethanol to give the product m.p. 85°–87° C.

Yield 6.2 g, 14%
TLC (Chloroform) Rf 0.6
IR (Nujol) 1710 cm$^{-1}$

EXAMPLE 2

Preparation of an inclusion compound sucrose benzoate and monocrotofos.

Sucrose benzoate (20 g) is heated to about 110° C. to give a mobile molten phase. Monocrotofos (technical grade) 5 g (equivalent to 4 g pure) is added and the resultant molten mixture (which is very mobile at this temperature) is stirred vigorously for several minutes to ensure effective mixing of the two components, which appear miscible under these conditions. Agitation is stopped and the molten mixture is allowed to cool to room temperature. The resultant solid mass is ground to pass 50 micron screen and is washed several times with either water or cold ethanol to remove excess monocrotofos (i.e. monocrotofos which is not formally included, but rather which is merely adhering to the outside surfaces of the host particles). The final product, after drying in air at room temperature, is typically a cream coloured, free flowing powder, with a mean particle diameter of about 25 microns, water insoluble and with monocrotofos content of about 13% (pure basis).

This material may then be formulated to enable it to be sprayed in an aqueous medium.

EXAMPLE 3

Preparation of an inclusion compound of glucose penta-palmitate and monocrotofos.

Glucose penta-palmitate (20 g) and monocrotofos (5 g) are treated as described in Example 2. The final product, after washing with either water or cold ethanol, is an off-white, free flowing powder, with similar particle size as the product described in Example 10. The final product contains about 4% monocrotofos.

EXAMPLE 4

Bioactivity of the inclusion compound of sucrose benzoate and monocrotofos.

The compound produced according to Example 2 is formulated by the addition of wetting agents, detergents and other emulsifying agents so that it forms a stable suspension, effectively dispersed in water. Leaves of cotton, soya and tomato plants are sprayed to run-off or dipped in suspensions of the above at concentrations (of active ingredient) of 200, 100, 50, 25, 12, 6, 3, 1.5 and 0.8 ppm.

On drying in air, the leaves are infested in separate biassays with larvae of *Heliothis armigera* in both the first instar (neonate) and 4th instar stages of development.

The infested leaves are closed (but not hermetically sealed) in small clear plastic vials and held in a controlled environment (23° C., 50% relative humidity) with normal diurnal variations of light and darkness. Mortality was assessed after 5 days for the first instar larvae and after 3 days for the fourth instar larvae.

Figure 2:
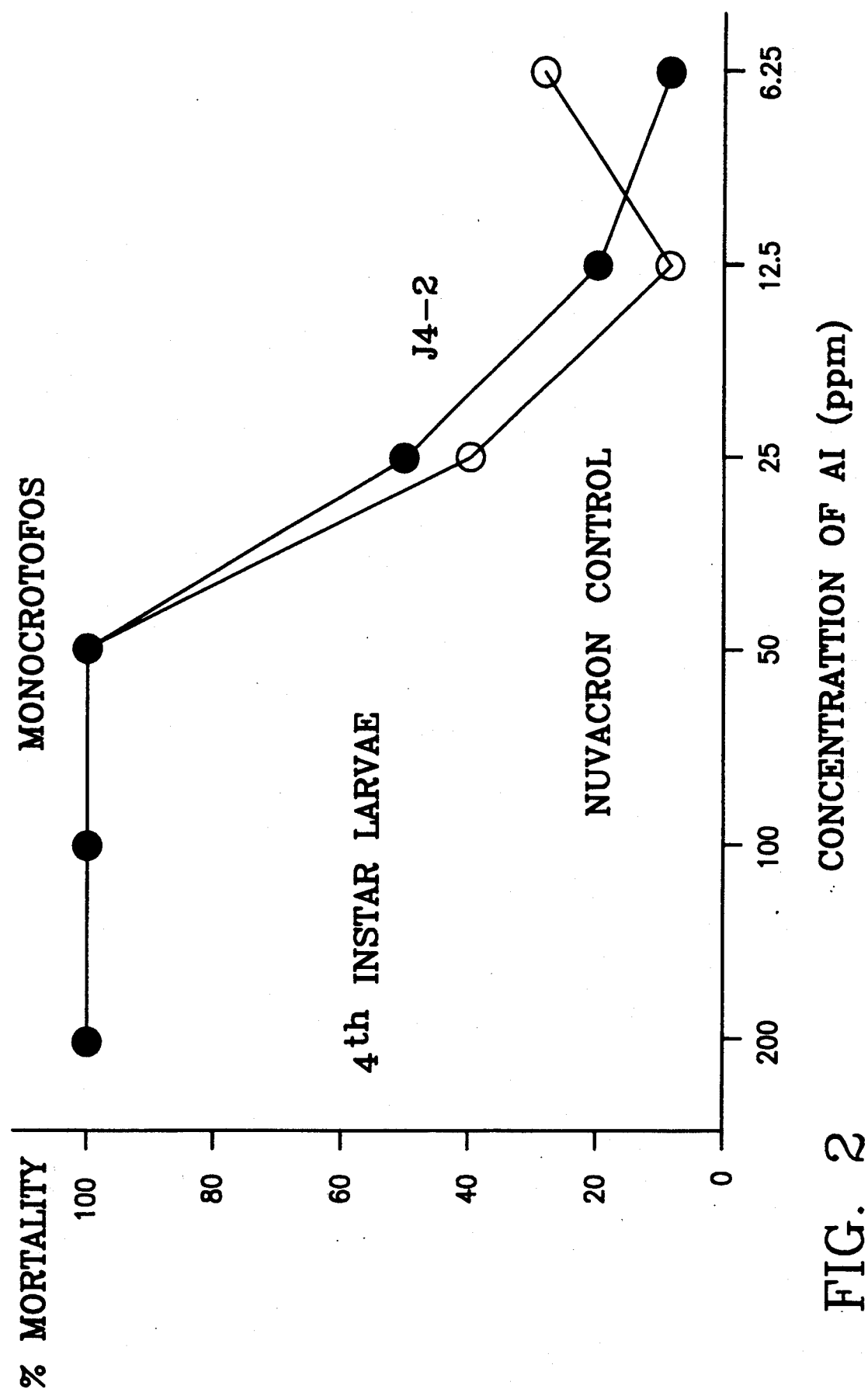

The mortality rates are shown in FIGS. 1 and 2 which show a plot of mortality rate (%) against the concentration (ppm) of the active ingredient (AI) for the first instar (neonate) larvae (FIG. 1) and the fourth instar larvae (FIG. 2).

EXAMPLES 5

Preparation of Mannitol hexa (Palmitate)

Mannitol (5.46 g, 0.03 mol) was suspended in pyridine (40 mL) and chloroform (5 mL) in an ice bath. Palmitoyl chloride (57.8 g, 0.21 mol) was added slowly with stirring. The precipitated solid was filtered, dissolved in chloroform and washed several times with water. The orgnaic layer was dried over anhydrous $Na_2SO_4$ and the solvent removed under reduced pressure to give a viscous orange syrup which was crystallised from chloroform/methanol. Recrystallisation from the same solvent mixture gave the product m.p. 59°–61° C. (Lit. 64° C.).

Yield 19 g, 40%
TLC (Chloroform) single spot Rf 0.8
IR (Nujol) 1740 $cm^{-1}$

EXAMPLES 6 to 10

The indicated compounds were each prepared by a method similar to that described in Example 1, from the appropriate sugar and acid anhydride.

EXAMPLE 6

β-D-Glucose penta (Cyclohexane Carboxylate)

mp 174°–176° C. Yield 6.7 g, 67%. TLC (90 Chloroform/10 Hexane) Rf 0.5 IR (Nujol) 1738 $cm^{-1}$.

EXAMPLE 7

Pentaerythritol tetra (Phenylacetate)

Coarse colourless needles, mp 72° C. Yield 7.8 g, 64%. TLC (97 $CHCl_3$/3 MeOH) Rf 0.6. IR (Nujol) 1730 $cm^{-1}$.

EXAMPLE 8

Pentaerythritol tetra (Phenylpropionate)

Fine long needles mp 49°–51° C. Yield 2.5 gm. 37%. TLC (97 $CHCl_3$/3 MeOH) Rf 0.75 IR (Melt) 1730 $cm^{-1}$.

EXAMPLE 9

Pentaerythritol Cyclohexanecarboxylate mp (MeOH/$CHCl_3$) 111° C., TLC ($CHCl_3$) Rf 0.7. IR 1735 $cm^{-1}$.

EXAMPLE 10

Mannitol hexa(Cyclohexane Carboxylate)

mp 135°–140° C. Yield 3.24 g, 43%. TLC (50 MeOH/50 $CHCl_3$) gave a single spot Rf 0.8. IR (Nujol) 1735 $cm^{-1}$.

EXAMPLE 11

Preparation of Adducts

Adducts of the compounds of Examples 5 to 10 with the active ingredients monocrotophos and methacrifos were prepared by one of two methods:

(1) Crystallisation, whereby the host and guest were dissolved in a suitable solvent, and the solvent removed slowly under reduced pressure at a moderate temperature (ca. 50° C.). Effective mixing was maintained during this procedure.

(2) Fusion, involving mixing of the solid host with the solid guest and the melting of the resulting composite. The molten mixture was stirred vigorously to promote homogeneity and allowed to cool at room temperature. The resulting solidified mass was ground up.

In each case, the solid products were collected and washed with water (in the case of monocrotophos) and with 80% aqueous methanol (in the case of methacrifos) to remove any active ingredient adhering to the outside surfaces of the adducts.

The content of active ingredient was determined using HPLC methods for monocrotophos and GLC methods for methacrifos.

EXAMPLE 12

Biological Efficacy of Adducts

The biological efficacy of adducts prepared according to Example 11 was determined as follows:

Freshly-picked cotton leaves were dusted with the adduct, which had been ground to pass a 50 micron screen. The bioassay was conducted using larvae of Heliothis armigera (4th instar).

For the purposes of evaluation, it was assumed that the distribution of adduct over the surface of the leaf was uniform, although this was clearly an approximation. Larvae were selected to be of similar size and weight (30–40 mg) and the leaf area was constant (10 $cm^2$). It was assumed that the amount of leaf eaten by the larvae was a direct measure of the amount of active ingredient ingested.

Results obtained for the adducts thus assayed are summarised in Table 1.

Notwithstanding the fact that the uneven coverage of the leaf by the adduct prevents more precise interpretation of the data, some interesting observations can be made.

In several cases, insect mortality was maximum even when little or no eating was observed. This mortality was seen to occur very quickly, suggesting poisoning of the larvae by contact.

TABLE 1

| | (see Key to Headings Below) | | | | | |
|---|---|---|---|---|---|---|
| Example | (1) | (2) | (3) | (4) | (5) | (6) |
| 1 | cryst. | mono | 0.338 | 30 | 0.102 | 70 |
|  | cryst. | methac | 0.576 | <1 | 0.006 | 100 |
| 5 | cryst. | mono | 0.019 | 30 | 0.006 | 30 |
| 6 | cryst. | mono | 0.013 | 5 | 0.0006 | 100 |
|  | cryst. | methac | 0.296 | <1 | 0.003 | 100 |
| 7 | cryst. | mono | 0.014 | 5 | 0.0007 | 100 |
| 8 | cryst. | mono | 0.017 | 20 | 0.003 | 90 |
|  | cryst. | methac | 0.198 | 2 | 0.006 | 100 |
| 9 | fusion | mono | 0.018 | <1 | 0.0002 | 100 |
|  | fusion | methac | 0.021 | <1 | 0.001 | 100 |
| 10 | fusion | mono | 0.087 | <1 | 0.0009 | 100 |
|  | fusion | methac | 0.082 | 20 | 0.016 | 80 |

Key to Table Headings
(1) Method of forming adduct. cryst. = crystallisation
(2) Active ingredient. mono = monocrotophos; methac = methacrifos
(3) Quantity of active ingredient applied (% of body weight)
(4) Leaf consumed (%)
(5) Quantity of active ingredient presumed ingested (% of body weight)
(6) Mortality (%)

I claim:

1. A pesticidal material which comprises an inclusion compound or molecular complex of a pesticide and a host molecule, characterised in that the host molecule is a mono-, oligo- or poly-saccharide ester.

2. A pesticidal material as claimed in claim 1, characterised in that the host molecule is a carboxylic ester of a mono-, oligo- or poly-saccharide.

3. A pesticidal material as claimed in claim 1, characterised in that the host molecule is
β-D-Glucose (penta) myristate;
Mannitol (hexa) palmitate;
Pentraerythritol (tetra) palmitate;
β-D-Glucose (penta) palmitate;
Pentaerythritol (tetra) monosuccinate;
Pentaerythritol (tetra) benzoate;
Sucrose (octa) benzoate;
Mannitol (hexa) benzoate;
β-D-Glucose (penta) cyclohexane carboxylate;
Pentaerythritol (tetra) phenylacetate;
Pentaerythritol (tetra) cyclohexane carboxylate; or
Mannitol (hexa) cyclohexane carboxylate.

4. A pesticidal material as claimed in claim 1, characterised in that the host molecule is a sucrose benzoate.

5. A pesticidal material as claimed in claim 1, characterised in that the pesticide is chlorpyrifos, dichlorvos, fenthion, fenthion ethyl, fenitrothion, fonofos, methacriphos, methomyl, monocrotofos, phoxim, trithion, fenvalerate, permethrin or cypermethrin.

6. A pesticidal composition, characterised in that it comprises as an active ingredient a pesticidal material as claimed in claim 1.

7. A method for combating insect pests, characterised in that a pesticidal material or composition as claimed in claim 1 is applied to the insects or their locus.

8. A pesticidal material as claimed in claim 3 wherein the pesticide is chlorpyrifos, dichlorvos, fenthion, fenthion ethyl, fenitrothion, fonofos, methacriphos, methomyl, monocrotofos, phoxim, trithion, fenvalerate, permethrin or cypermethrin.

9. A pesticidal material of claim 1 which comprises a substantially water insoluble inclusion compound or molecular complex of (a) a pesticide and (b) a host molecule, wherein the host molecule is a mono-, oligo- or poly-saccharide ester.

10. A pesticidal material as claimed in claim 9 wherein:
(a) the pesticide is chlorpyrifos, dichlorvos, fenthion, fenthion ethyl, fenitrothion, fonofos, methacriphos, methomyl, monocrotofos, phoxim, trithion, fenvalerate, permethrin or cypermethrin; and
(b) the host molecule is β-D-glucose (penta) myristate; mannitol (hexa) palmitate; pentaerythritol (tetra) palmitate; β-D-glucose (penta) palmitate; pentaerythritol (tetra) monosuccinate; pentaerythritol (tetra) benzoate; sucrose (octa) benzoate; mannitol (hexa) benzoate; β-D-glucose (penta) cyclohexane carboxylate; pentaerythritol (tetra) phenylacetate; pentaerythritol (tetra) cyclohexane carboxylate; or mannitol (hexa) cyclohexane carboxylate.

* * * * *